(12) United States Patent
Roehn

(10) Patent No.: US 11,781,557 B2
(45) Date of Patent: *Oct. 10, 2023

(54) RADIALLY COMPRESSIBLE AND EXPANDABLE ROTOR FOR A FLUID PUMP

(71) Applicant: ECP Entwicklungsgesellschaft mbH, Aachen (DE)

(72) Inventor: Daniel Roehn, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,153

(22) Filed: Jul. 22, 2022

(65) Prior Publication Data

US 2023/0045694 A1 Feb. 9, 2023

Related U.S. Application Data

(63) Continuation of application No. 16/725,703, filed on Dec. 23, 2019, now Pat. No. 11,434,922, which is a (Continued)

(30) Foreign Application Priority Data

Dec. 23, 2009 (EP) .................................. 09075572

(51) Int. Cl.
*F04D 29/24* (2006.01)
*F04D 29/60* (2006.01)
(Continued)

(52) U.S. Cl.
CPC ......... *F04D 29/247* (2013.01); *A61M 60/205* (2021.01); *A61M 60/216* (2021.01);
(Continued)

(58) Field of Classification Search
CPC .... F04D 29/247; F04D 29/607; A61M 60/13; A61M 60/135; A61M 60/148;
(Continued)

(56) References Cited

U.S. PATENT DOCUMENTS 3,510,229 A   5/1970  Smith
3,568,659 A   3/1971  Karnegis
(Continued)

FOREIGN PATENT DOCUMENTS

CA   1008330 A    4/1977
CA   2311977 A1  12/2000
(Continued)

OTHER PUBLICATIONS

International Search Report and Written Opinion for International Application No. PCT/EP2010/007996 dated Mar. 15, 2011.
(Continued)

*Primary Examiner* — Brian O Peters
(74) *Attorney, Agent, or Firm* — Botos Churchill IP Law LLP

(57) ABSTRACT

In a rotor for a fluid pump which is made radially compressible and expandable and has a hub and at least one conveying element which has a plurality of struts and at least one membrane which can be spanned between them, provision is made for a design in accordance with the invention which is as simple and inexpensive as possible that at least one first group of struts is pivotable in a pivot plane, starting from a common base, and can thus be spanned open in the manner of a fan, wherein the conveying element lies along the hub and contacts it over its full length in the expanded state to avoid a pressure loss at the margin of the conveying element between it and the hub and thus to realize an optimum efficiency.

15 Claims, 5 Drawing Sheets

Related U.S. Application Data continuation of application No. 15/869,285, filed on Jan. 12, 2018, now Pat. No. 10,557,475, which is a continuation of application No. 15/142,292, filed on Apr. 29, 2016, now Pat. No. 9,903,384, which is a continuation of application No. 13/261,315, filed as application No. PCT/EP2010/007996 on Dec. 23, 2010, now Pat. No. 9,339,596.

(60) Provisional application No. 61/289,569, filed on Dec. 23, 2009.

(51) Int. Cl.
  *A61M 60/422* (2021.01)
  *A61M 60/414* (2021.01)
  *A61M 60/808* (2021.01)
  *A61M 60/216* (2021.01)
  *A61M 60/237* (2021.01)
  *A61M 60/205* (2021.01)
  *A61M 60/148* (2021.01)
  *A61M 60/13* (2021.01)
  *A61M 60/135* (2021.01)

(52) U.S. Cl.
  CPC ........ *A61M 60/237* (2021.01); *A61M 60/414* (2021.01); *A61M 60/422* (2021.01); *A61M 60/808* (2021.01); *F04D 29/607* (2013.01); *A61M 60/13* (2021.01); *A61M 60/135* (2021.01); *A61M 60/148* (2021.01)

(58) Field of Classification Search
  CPC .............. A61M 60/205; A61M 60/216; A61M 60/237; A61M 60/414; A61M 60/422; A61M 60/808
  See application file for complete search history.

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,681,512 A * | 7/1987 | Barnard .................. F03D 3/067 416/240 |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | Mckenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,151,721 A | 9/1992 | Allendorf et al. |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A * | 5/1998 | Reitan .................. A61M 60/414 604/151 |
| 5,755,784 A | 5/1998 | Jarvik |
| 5,776,190 A | 7/1998 | Jarvik |
| 5,813,405 A | 9/1998 | Montano et al. |
| 5,820,571 A | 10/1998 | Erades et al. |
| 5,851,174 A | 12/1998 | Jarvik et al. |
| 5,877,566 A | 3/1999 | Chen |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nuesser et al. |
| 6,790,171 B1 | 9/2004 | Gruendeman et al. |
| 6,860,713 B2 | 3/2005 | Hoover |
| 6,945,977 B2 | 9/2005 | Demarais et al. |
| 6,981,942 B2 * | 1/2006 | Khaw .................. A61M 60/825 623/3.13 |
| 7,022,100 B1 | 4/2006 | Aboul-hosn et al. |
| 7,027,875 B2 | 4/2006 | Siess et al. |
| 7,054,156 B2 | 5/2006 | Espinoza-ibarra et al. |
| 7,074,018 B2 | 7/2006 | Chang |
| 7,179,273 B1 | 2/2007 | Palmer et al. |
| 7,393,181 B2 | 7/2008 | Mcbride et al. |
| 7,467,929 B2 | 12/2008 | Nuesser et al. |
| 7,731,675 B2 | 6/2010 | Aboul-hosn et al. |
| 7,841,976 B2 | 11/2010 | Mcbride et al. |
| 7,927,068 B2 | 4/2011 | Mcbride et al. |
| 7,934,909 B2 | 5/2011 | Nuesser et al. |
| 8,079,948 B2 | 12/2011 | Shifflette |
| 9,028,392 B2 * | 5/2015 | Shifflette ............. A61M 60/226 600/16 |
| 11,434,922 B2 * | 9/2022 | Roehn .................. F04D 29/607 |
| 2002/0094273 A1 | 7/2002 | Huang |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2005/0101200 A1 | 5/2005 | Townsend |
| 2006/0008349 A1 | 1/2006 | Khaw |
| 2006/0062672 A1 | 3/2006 | Mcbride et al. |
| 2006/0195004 A1 | 8/2006 | Jarvik |
| 2007/0270875 A1 | 11/2007 | Bacher et al. |
| 2008/0073983 A1 | 3/2008 | Krajcir |
| 2008/0103591 A1 | 5/2008 | Siess |
| 2008/0114339 A1 | 5/2008 | Mcbride et al. |

(56) References Cited

U.S. PATENT DOCUMENTS

| | | |
|---|---|---|
| 2008/0132747 A1 | 6/2008 | Shifflette |
| 2008/0132748 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | Mcbride et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0071338 A1 | 3/2011 | Mcbride et al. |
| 2011/0236210 A1 | 9/2011 | Mcbride et al. |
| 2011/0238172 A1 | 9/2011 | Akdis |
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0364293 A2 | 4/1990 |
| EP | 480102 A1 | 4/1992 |
| EP | 560000 A2 | 9/1993 |
| EP | 629412 A2 | 12/1994 |
| EP | 768091 A1 | 4/1997 |
| EP | 884064 A2 | 12/1998 |
| EP | 914171 A2 | 5/1999 |
| EP | 0916359 A1 | 5/1999 |
| EP | 951302 A2 | 10/1999 |
| EP | 1019117 A1 | 7/2000 |
| EP | 1066851 A1 | 1/2001 |
| EP | 1114648 A2 | 7/2001 |
| EP | 1337288 A1 | 8/2003 |
| EP | 1061968 B1 | 8/2005 |
| EP | 1651290 A1 | 5/2006 |
| EP | 2047872 A1 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| GB | 2405677 A | 3/2005 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 9944651 A1 | 9/1999 |
| WO | 0027446 A1 | 5/2000 |
| WO | 0043054 A2 | 7/2000 |
| WO | 0062842 A1 | 10/2000 |
| WO | 2001007760 A1 | 2/2001 |
| WO | 2001007787 A1 | 2/2001 |
| WO | 2001083016 A2 | 11/2001 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006051023 A1 | 5/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A2 | 10/2008 |
| WO | 2008137352 A1 | 11/2008 |
| WO | 2008137353 A1 | 11/2008 |
| WO | 2009015784 A1 | 2/2009 |
| WO | 2009029959 A2 | 3/2009 |
| WO | 2009073037 A1 | 6/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

(56) References Cited

OTHER PUBLICATIONS

Office Action from corresponding German Application No. 11 2010 004 977.7 dated May 9, 2022 (10 pages).

* cited by examiner

RADIALLY COMPRESSIBLE AND EXPANDABLE ROTOR FOR A FLUID PUMP

CROSS-REFERENCE TO RELATED APPLICATIONS

This application is a continuation of U.S. patent application Ser. No. 16/725,703, filed Dec. 23, 2019, allowed, which is a continuation of U.S. patent application Ser. No. 15/869,285, filed Jan. 12, 2018, now U.S. Pat. No. 10,557, 475, issued on Feb. 11, 2020, which is a continuation of U.S. patent application Ser. No. 15/142,292, filed Apr. 29, 2016 now U.S. Pat. No. 9,903,384, issued on Feb. 27, 2018, which is a continuation of U.S. patent application Ser. No. 13/261, 315, filed Jul. 26, 2012 now U.S. Pat. No. 9,339,596, issued on May 17, 2016, which entered the national stage on Jul. 26, 2012 and which is a United States National Stage filing under 35 U.S.C. § 371 of International Application No. PCT/EP2010/007996, filed Dec. 23, 2010, which claims the benefit of U.S. Provisional Patent Application No. 61/289, 569, filed Dec. 23, 2009, and European Patent Application No. 09075572.9, filed Dec. 23, 2009, the contents of all of which are incorporated by reference herein in their entirety. International Application No. PCT/EP2010/007996 was published under PCT Article 21(2) in English.

BACKGROUND OF THE INVENTION

The present invention is in the field of mechanical engineering and microengineering and in particular relates to conveying devices for liquids and fluids in general.

Such conveying devices are already known in the most varied manifestations as pumps using different conveying principles. Rotary drivable pumps are particularly interesting in this connection which have rotors which convey fluids radially or axially.

In this respect, the most varied demands are made on such pumps as regards the mounting of the rotor, the resistance toward environmental influences and the interactions with the fluids to be conveyed. In particular on the conveying of fluids having complex, biologically active molecules, e.g. inside living bodies, special demands must be made on the relative speed between corresponding conveying elements and the fluid as well as turbulence and shear forces.

BRIEF SUMMARY OF THE INVENTION

A particular field for such pumps is in the field of microengineering in the use in invasive medicine where pumps are manufactured in such small construction that they can be moved through vessels of the body and brought to their site of operation.

Such pumps are already known in a function as heart-assisting pumps which can be conducted, for example, through blood vessels in a patient's body up to and into a ventricle and can be operated there.

To optimize the efficiency of such pumps, it is also already known to equip these pumps with compressible and expandable rotors which are radially compressed during the transport through a blood vessel and can only be expanded within a larger body space, for example in a ventricle.

The construction demands on such compressible and expandable rotors are in particular very high due to the small construction and to biocompatibility as well as due to the demands on the reliability.

A corresponding compressible rotor is known, for example, from U.S. Pat. No. 6,860,713. Another pump of this kind is known from U.S. Pat. No. 7,393,181 B2.

In this respect, it is customary for the compressibility of the rotors to use either elastically or superelastically deformable bodies or structures, for example of so-called memory alloys such as nitinol which are optionally covered by a membrane so that corresponding rotors can be easily radially elastically compressed and can be expanded or erected automatically or with the aid of pulling mechanisms for operation.

Rotors are also known which can be expanded in operation. by the counter-pressure of the fluid or by centrifugal forces.

The most varied mechanisms are moreover known in accordance with which blades can be folded, bended or radially placed down in a similar manner at corresponding hubs.

With such complex constructions, it. must be ensured that the conveying surfaces of a corresponding conveying element are as smooth as possible to achieve a high efficiency, that the conveying surface can be optimized in the angle with respect to the axis of rotation and that the speed of rotation can be selected in a meaningful range.

In addition, the compression and expansion mechanism must be given a safe design such that it works reliably, such that the pump has a stable state in operation and such that the pump can be reliably compressed and transported in the compressed state.

The underlying object of the present invention against the background of these demands and of the prior art is to provide a pump of this kind which works reliably and which can be simply and reliably compressed and expanded with a good degree of efficiency.

The object is achieved in accordance with the invention by the features of claim 1.

To provide a radially compressible and expandable rotor for a fluid pump having a hub and at least one conveying element which comprises a plurality of struts and at least one membrane which can be spanned between them; and to make the corresponding rotor compressible and expandable in a particularly simple and reliable manner, the invention provides that at least one first group of struts is pivotable, starting from a common base, in a pivot plane and can thus be spanned in the manner of a fan and that, in the expanded state, the conveying element lies along the hub and contacts it over its full length.

The surface of the conveying element is thus formed by the membrane spanned between the struts and said membrane can be folded together like a fan for transport, with the struts taking up much less room radially in the folded state than in the spanned open state. The word "fan" here designates the basically two-dimensional structure, in the meaning of the German. word "Fächer", that preferably looks like a classical Chinese or Spanish fan, i.e. preferably a structure consisting of a plurality of linear struts held together at one end but free to move apart at the other. At least some of the struts, in particular all the struts, can be run together in the manner of a fan at a common base and can be pivotally mounted in a simple form there. In this case, the struts can then be spanned open for the spanning of the conveying element completely to one side of the hub at a fan angle of 90° or at both sides up to the hub, for example, at an angle of 180° so that the conveying element ideally contacts the hub at both sides of the base. A particularly good efficiency in the conveying of fluids is realized in that pressure compensation processes of the fluid between the conveying element and the hub are minimized.

To minimize the space requirements of the conveying element or of a plurality of conveying elements if two or more conveying elements are provided at the hub, in the compressed state, for example during the transport of the fluid pump, provision can advantageously be made that the hub has a first cutout in which at least the first group of struts, or all the struts, is/are received at least partly in the compressed state. The hub can in this respect generally be cylindrical or cylindrically symmetrical.

In this manner, a contour of the hub is realized which radially projects very little, which is also smooth in dependence on the proportion of struts which can be accommodated within the cut-out and which makes possible a simple displacement, for example within a blood vessel.

A common pivot axis of a plurality of struts can advantageously also be arranged in the region of the first cut-out. In this case, the struts can easily be outwardly pivoted out of the cut-out for the operation of the pump at the site of operation.

A particularly space-saving effect is possible when the pivot axis passes through the first cut-out and extends tangentially to the peripheral direction of the hub. In this case, the pivotable part of the struts can be outwardly pivoted out of the cut-out, whereas a region of the struts at the struts in each case disposed opposite the mounting point is movable within the cut-out.

It can prove to be particularly advantageous if two conveying elements each having a group of struts which can be spanned open like a fan are provided which are disposed opposite one another at the periphery of the hub and are at least partly accommodated in a cut-out of the hub in particular in the compressed state. In this case, two conveying elements can be arranged symmetrically at the hub to achieve a good efficiency. Depending on the shape of the conveying elements, which can be provided as planar surfaces slanted with respect to the rotor axis, for example, or which can also have a spiral shape, provision can be made to allow different conveying elements to revolve about the hub offset with respect to one another.

In this respect, a plurality of cut-outs can be provided at the periphery of the hub, with the presence of two conveying elements, two cut-outs, for example, which can be diametrically opposite one another at the periphery of the hub and which can, for example, also be combined to a throughgoing opening of the hub. The cut-out in the hub can thus be manufactured particularly simply from a technical production aspect and sufficient room also results for a pivot movement of the struts within the cut-out.

Provision can moreover advantageously be made that each of the conveying elements lies along the hub in each case in the expanded state and contacts it at both sides of the respective cut-out. In this case, the struts of the conveying element at pivotable so far at both sides that they cover an angle of 180° along the hub and cover axially at both sides of the cut-out, provided such a cut-out is provided, or of a corresponding pivot point, provided the conveying element is mounted at the hub surface, and tightly contact the peripheral surface of the hub.

To achieve an ideal axial conveying and a good efficiency of the rotor, provision is advantageously provided that the membrane is inclined at least sectionally with respect to the rotor axis in the expanded state. In this respect, depending on the angle which the membrane or the conveying surface of the conveying element adopts with respect to the longitudinal rotor axis, a spiral rotation of the membrane about the hub can also be provided. A planar form of the membrane can, however, also be provided.

An advantageous embodiment of the invention can also provide that at least one strut is angled outward out of the pivot plane of the struts at least over a part of its length with respect to further struts.

Any desired fluidically favorable three-dimensional shape of the membrane/conveying surface of the conveying element, which is favorable for the conveying efficiency, can be realized by the angling or bending of individual or groups of struts. The struts can, for example, be correspondingly curved or angled at their ends disposed opposite the pivot axis or over the half of their length further remote from the pivot axis in order not to make a dipping into the cut-out of the hub more difficult or to impede it in the region of the pivot axis.

A particularly simple embodiment of the rotor in accordance with the invention provides that at least the struts of the respective group which can be spanned open in the manner of a fan are pivotably mounted on a shaft within the respective cut-out. The provision of a corresponding shaft in the cut-out represents a particularly simple and permanent solution for the pivotable mounting of the struts.

Provision, can, however, also be made that the pivotable struts are connected to one another by film hinges at their base. For example, the struts can be manufactured from the same material and can be made contiguously in one piece, for example from an injection molded material. In this case, the membrane can, for example, be applied in the dipping method by dipping the struts into a liquid plastic, for example polyurethane; it is, however, also conceivable to manufacture the membrane from the same material as the struts with a corresponding design of the thickness of the membrane. In this case, the provision of film hinges can be realized by weakening the material in the regions which are wanted to be correspondingly flexible.

To provide an ideal outer contour of the conveying element, it can be useful or necessary to combine different struts with different lengths with one another within the conveyor element. The corresponding length design of the struts can also, for example, depend on how the housing is shaped in which the rotor moves.

In addition, to increase the efficiency and to improve the stability of the rotor in operation, at least one reception apparatus, for example a rail, for receiving the external struts of the conveying element in the expanded state can be provided along the hub.

Accordingly, after the expansion and the fan-like spanning open of the struts or after the spanning of the membrane, the outermost struts, which extend approximately parallel to the hub in one or both directions axially, starting directly from the base, can be fixed in a respective one of such reception apparatus which can, for example, be made in fork-like form. The respective outer strut can be laid at the hub in such a fork. A different form of fixing of the struts to the hub can also take place, such as by magnets or by insertion into a rail-like cut-out or elevated portion of the hub.

It is thus ensured that the fluid to be conveyed cannot flow between the conveying element and the hub within the course of the pressure compensation processes and that, on the other hand, additional purchase and stability is given to the conveying element by the hub.

BRIEF DESCRIPTION OF THE DRAWINGS

The invention will be shown and subsequently described in more detail in the following with reference to an embodiment in a drawing. There are shown FIG. 1 schematically, a view of a fluid pump on use as a heart catheter pump.

DETAILED DESCRIPTION

Figure 1:
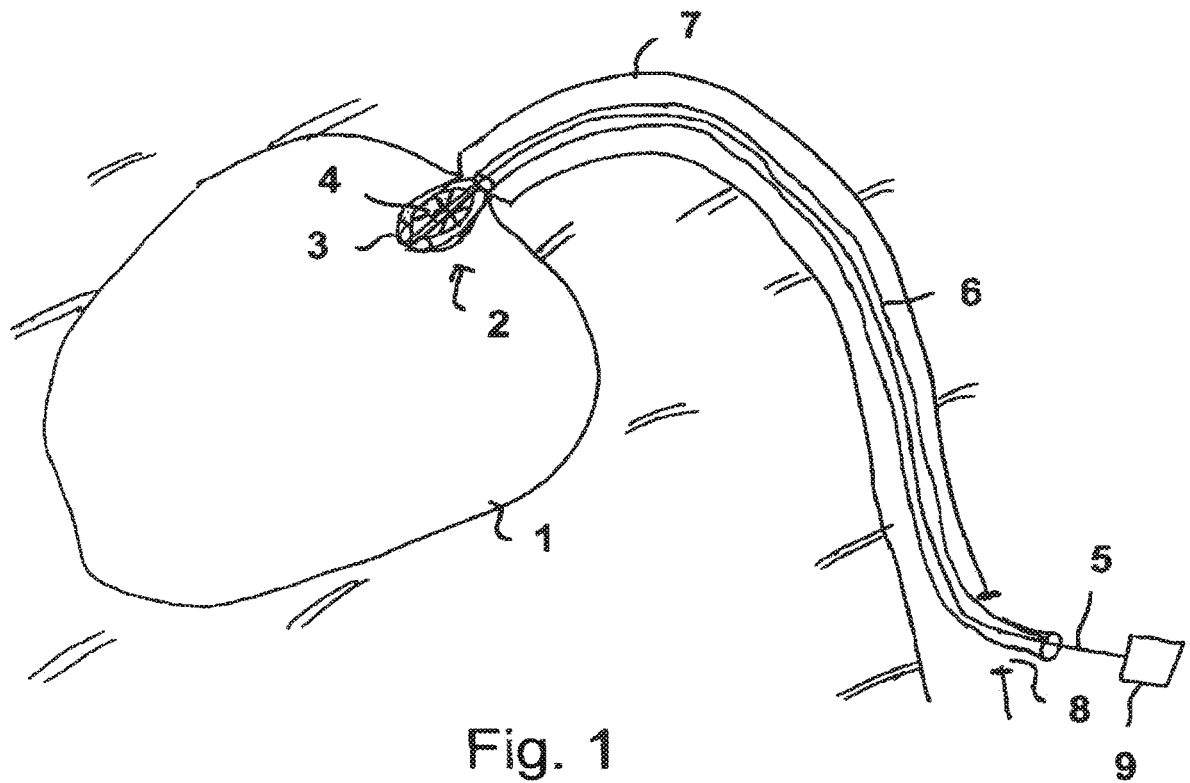

FIG. 1 schematically shows a fluid pump in which the rotor in accordance with the invention is used after the introduction into a ventricle 1. The pump 2 has a housing 3 as well as a hub 4 to which the conveying elements are fastened. The hub 4 is connected to a shaft 5 which is conducted through a hollow catheter 6 within a blood vessel 7 and is conducted out of it and the patient's body by a sluice 8. The rotatable shaft 5 can be driven at high revolutions, for example in the order of 10,000 r.p.m., by means of a motor 9.

Blood can be conveyed between the ventricle 1 and the blood vessel, for example sucked in by the pump 2 and pressed into the blood vessel 7, by means of the rotational movement transmitted onto the hub 4 and onto the conveying elements of the pump.

The pump 2 can have a diameter or general dimensions in the operating state which would be too large to be transported through the blood vessel 7. The pump is radially compressible for this purpose. It is shown in FIG. 1 in the expanded state which it can adopt after the introduction into the ventricle 1 by means of the hollow catheter 6.

The pump is pushed in the compressed state together with the hollow catheter 6 so far through the blood vessel 7 until it projects into the ventricle 1 before it is expanded.

The pump 2 has to be compressed again, which can be done, for example, by corresponding pulling elements, not shown in detail, before the removal, which takes place by pulling out the catheter 6, or, if the pump is only expanded by centrifugal forces, it is stopped and then collapses in on itself.

It is also conceivable to compress the pump at least a little by pulling it into the hollow catheter in that, for example, an introduction funnel is provided at the distal end of the hollow catheter 6.

Figure 2:
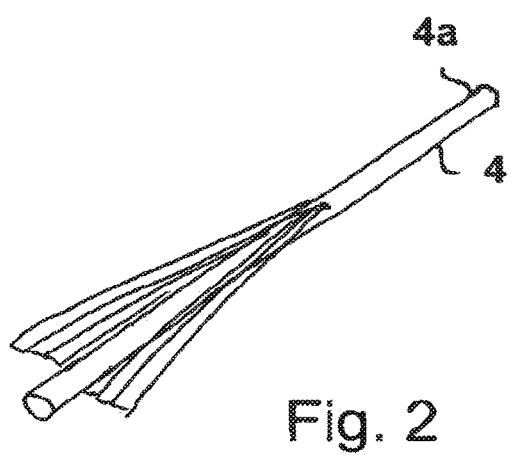
FIG. 2 a rotor in a view in the compressed state.

The design of the hub 4 is shown in more detail in FIG. 2, with the struts of the conveying element/elements being shown in the compressed state, i.e. in the state placed onto the hub. The front end of the hub, which faces the inner space of the ventricle 1, is marked by 4a.

The struts can be placed so tightly on the hub that they only take up a vanishingly small space in the radial direction of the rotor. The membrane is rolled or folded in between the struts in the compressed state.

Figure 3:
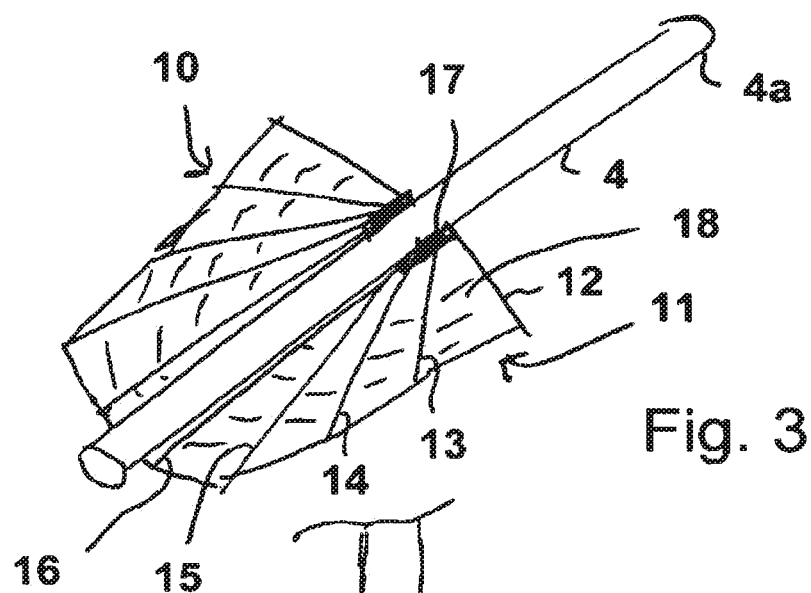
FIG. 3 an embodiment of a rotor in the expanded state.

FIG. 3 shows the at least partly expanded state of a rotor with the hub 4, with two conveying elements 10, 11 being provided which are disposed diametrically opposite one another at the periphery of the cylindrically formed hub 4. Each of the conveying elements generally has the shape of a quarter of an ellipse so that the individual struts 12, 13, 14, 15, 16 cover an angular range overall of approximately 90°, starting from the base 17. However, other shapes, for example also rectangular shapes, can be achieved by a different design of the length of the struts.

The membrane 18 is tautened flat and tight between the struts 12 to 16 in the expanded state. The conveying element 10 is exactly opposite the conveying elements 11 described in more detail so that both together form half an ellipse in interaction with the hub 4. The struts 16 contacting the hub 4 most closely can, for example, be fixed there by a reception apparatus or can at least be guided. Such a reception apparatus can, for example, be made in U shape with two limbs so that the strut 16 can dip into the conveying elements 11 on their expansion and is held there as required. It is thereby ensured that as good as no intermediate space arises between the strut 16 and the hub 4 which could cause a flowing off of the fluid between the hub and the conveying element and thus a pressure loss if it were present on the rotation of the rotor.

Figure 4:
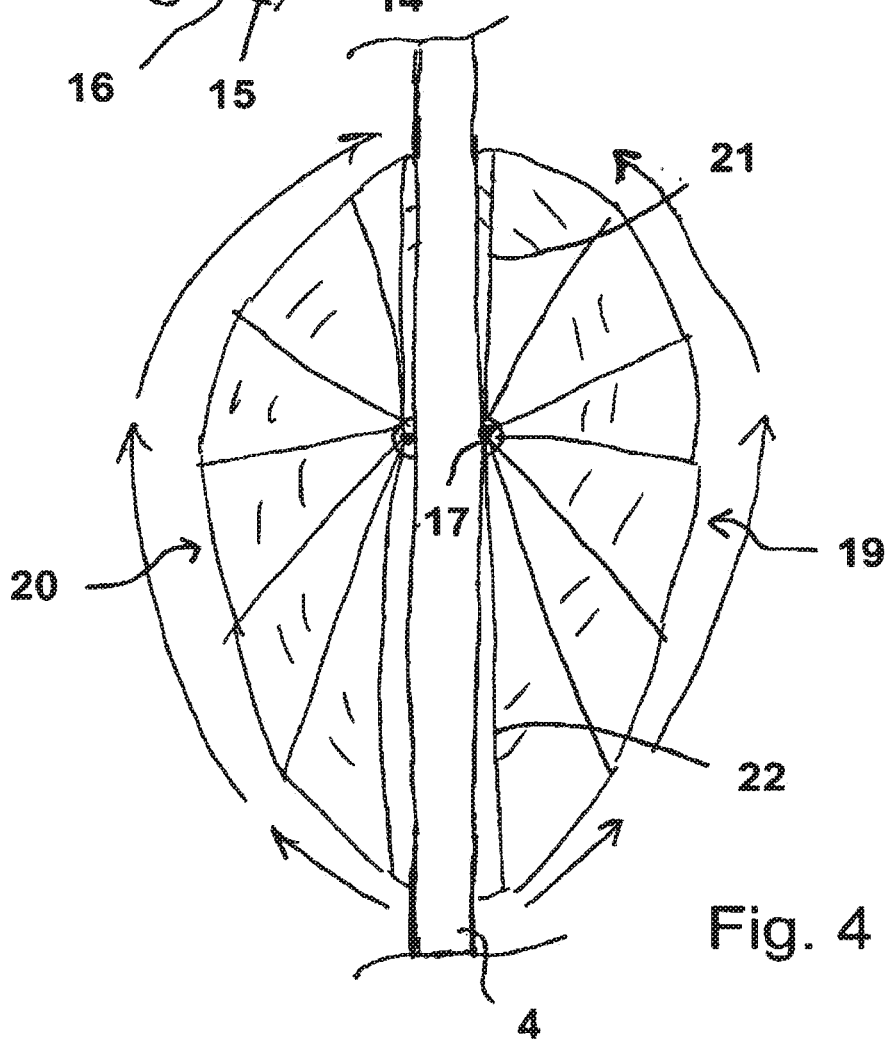
FIG. 4 a view of a further embodiment of a rotor in the expanded state.

FIG. 4 shows two semi-elliptical conveying elements 19, 20 which are disposed opposite one another at the periphery of the hub 4 which are made with the aid of the struts in the same way as shown in FIG. 3 and which axially contact the hub 4 axially at both sides of the respective base 17 such that a tight connection is present between the hub and the conveying element. Each of the conveying elements covers an angle of 180° in accordance with FIG. 4. Other shapes, for example, rectangular shapes, can also be achieved here by a different design of the length of the struts. The conveying elements of FIG. 4 can also be made in a similar manner from two respective conveying elements in accordance with FIG. 3, with in this case the respective pivot axes not having to be identical.

The struts of an individual conveying element 19, 20 are by all means of different length so that the base 17 does not have to lie axially at the center of the conveying element. As shown in FIG. 4, the strut 21 is, for example, shorter than the oppositely disposed strut 22.

The individual struts can, for example, be manufactured from a plastic in injection molding technology, e.g. can also be contiguous at the base 17, with a membrane being spanned between the struts, either by dipping the struts into a liquid plastic or by one-piece manufacture of the individual conveying elements 19, 20 in the whole from the same material, with the membrane then being provided as a film between the struts.

Figure 5:
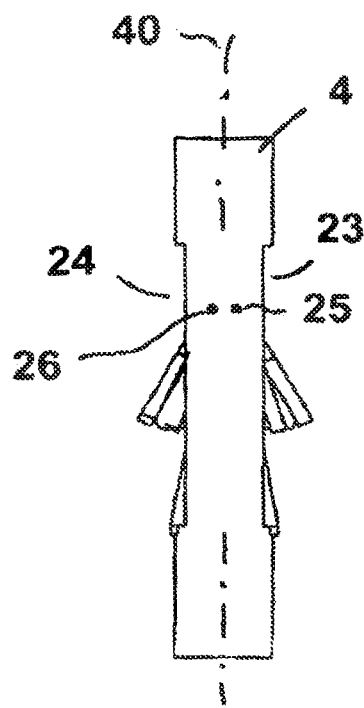
FIG. 5 a side view of a rotor in the compressed state.

FIG. 5 shows a side view of a hub 4 having two cutouts 23, 24 on both sides of the hub which are connected through the hub to form a common opening.

Two shafts 25, 26 on which the struts are pivotably mounted are fastened in this opening. The individual struts are substantially accommodated within the cutouts 23, 24 in the compressed state, as can be seen much more clearly in the view of FIG. 6 which is rotated by 90° about the axis of rotation 40 with respect to the representation of FIG. 5.

Figure 6:
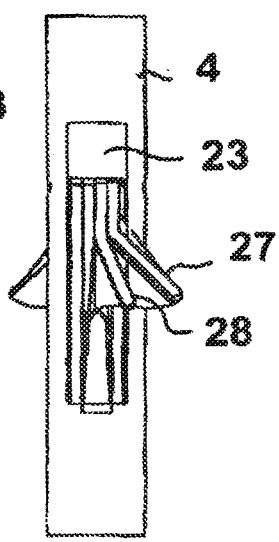
FIG. 6 a view of the arrangement of FIG. 5 rotated by 90° about the longitudinal rotor axis.

It moreover becomes clear from FIG. 6 that some of the struts 27, 28 are angled a little, at least at their respective ends remote from the pivot axis 25, 26, out of the common pivot plane of the struts which corresponds to the extent of the plane of the drawing in FIG. 5. This design of the struts has the consequence that the struts cannot be completely accommodated in the cut-outs 23, 24, but effects a three-dimensional, optimized design of the conveying element.

Figure 7:
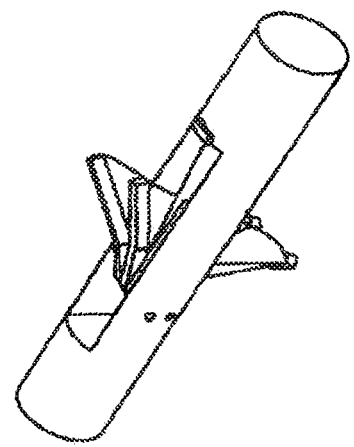
FIG. 7 a view as in FIGS. 5 and 6, shown three-dimensionally in an oblique view.

A three-dimensional representation of the rotor can be seen in FIG. 7 which clearly shows the ends of the struts which are angled in a projecting manner.

Figure 8:
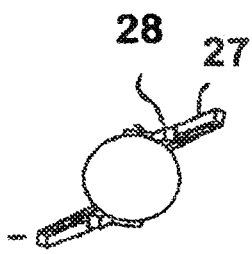
FIG. 8 the arrangement of FIGS. 5, 6 and 7 in an axial plan view of the rotor.

FIG. 8, which shows an axial plan view of the rotor of FIGS. 5 to 7, also clearly shows the projecting ends of the struts 27, 28 and of the struts of the further conveying element disposed opposite them.

Figures 9, 10, 11:
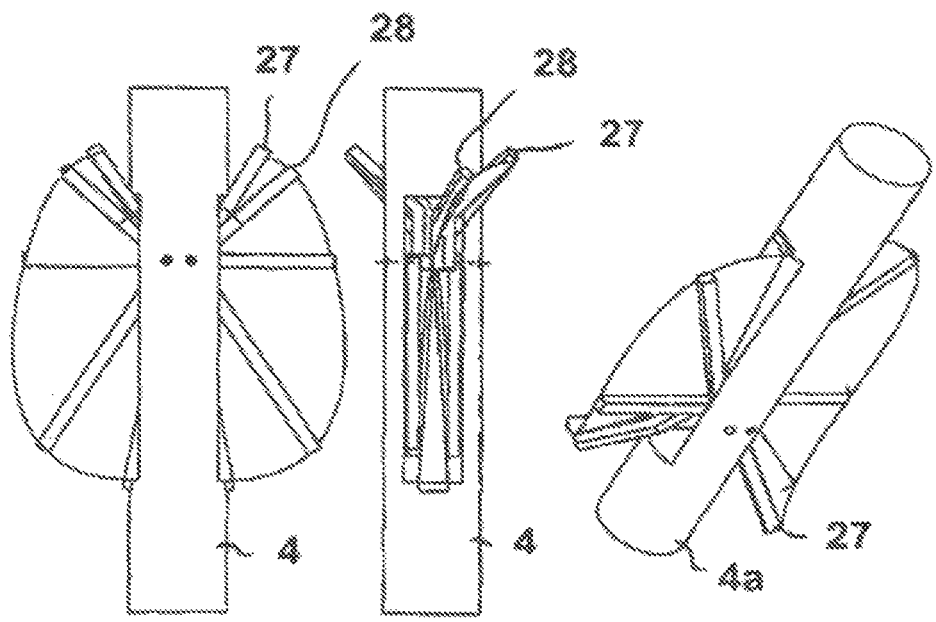
FIG. 9 a side view of the rotor of FIGS. 5 to 8 in the expanded state.
FIG. 10 the view of FIG. 9 rotated by 90° about the longitudinal axis of the rotor.
FIG. 11 an oblique view of the arrangement of FIGS. 9 and 10.

FIG. 9 shows in the expanded state of the rotor of FIGS. 5 to 8 how the angled struts 27, 28 effect a curvature of the front edge of the conveying element out of the plane of the membrane, whereby a structure of the conveying element results which is spiral in approach.

Figure 12:
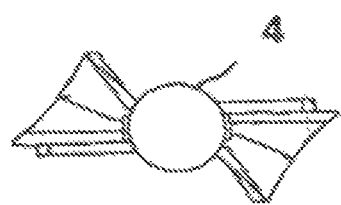
FIG. 12 an axial plan view of the rotor of FIGS. 9 to 11.

This can be seen particularly clearly from FIGS. 10 and 11 respectively. FIG. 12 also clearly shows in plan view that the membrane spanned between the struts is not present in a planar form, but is rather curved.

Figure 13:
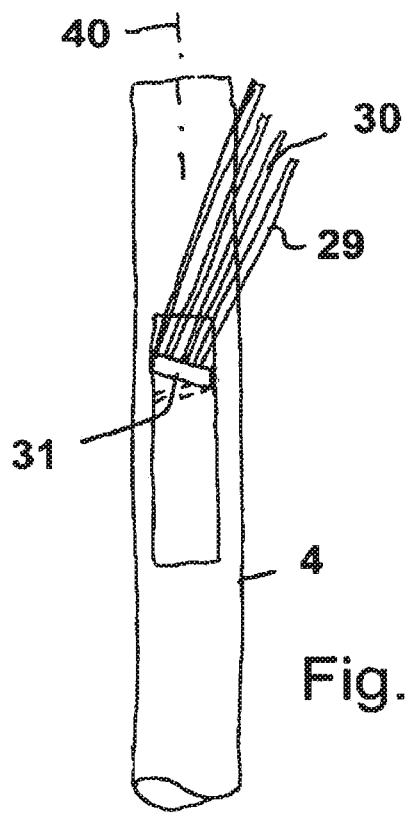
FIG. 13 a side view of a rotor with an inclined pivot plane of the struts.

FIG. 13 makes it clear with reference to another embodiment that the struts 29, 30 can also be slanted with respect to their pivot plane as regards the longitudinal axis/axis of rotation 40 of the hub 4. This is possible, for example, by a corresponding oblique position of the shaft 31 on which the struts 29, 30 are pivotably mounted, as shown in FIG. 13.

A spiral revolution of the conveying element/of the membrane about the hub 4 thus also results on the presence of a planar membrane between the struts 29, 30 so that an axial propulsion of the fluid to be conveyed arises on the rotation of the hub.

The respective other pivot axis which belongs to the oppositely disposed conveying element is then likewise slanted in mirror symmetry to the pivot axis 31.

Figure 14:
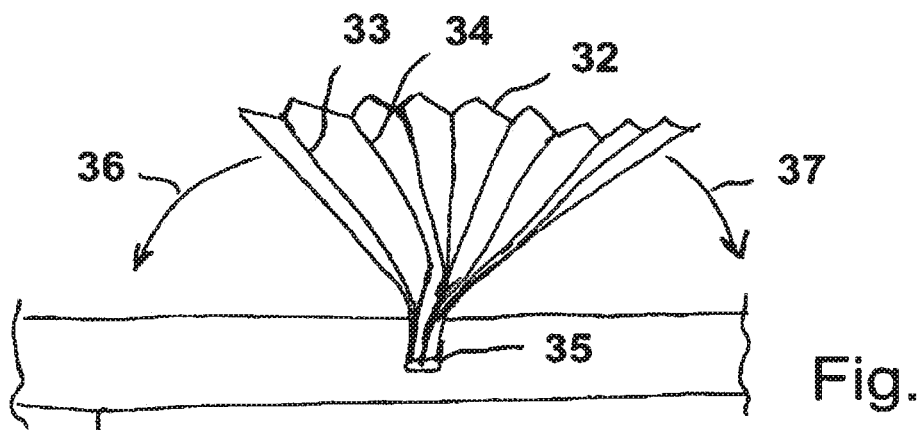
FIG. 14 a further embodiment with a fan and a fastening to the hub.

FIG. 14 shows a design of a conveying element 32 in the form of a folded membrane, with the individual kinks of the membrane which form the struts being marked by 33, 34. In the present example, the kinks are made in parallel. However, they can also be made at an angle to one another or curved.

The membrane can be clamped in a cut-out 35 of the hub 4 in the manner of a fan and can be folded in axially at both sides of the hub, with the membrane stretching. A particularly simple manner of manufacture for the conveying element thus results.

The arrows 36, 37 mark the folding movements of the conveying element to the hub 4 at both sides of the cut-out 35.

Figure 15:
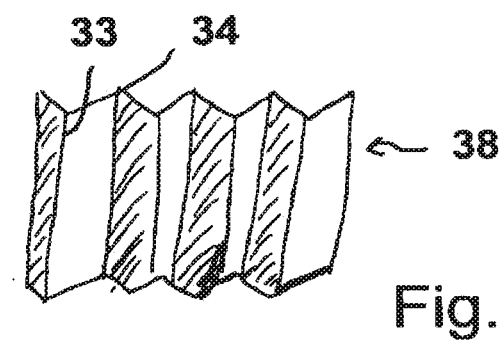
FIG. 15 a three-dimensional view of the conveying element as a folded membrane.

FIG. 15 shows the conveying element 38 again in isolated form as a kinked membrane with the kinks/struts 33, 34 before the installation into the cut-out 35 of the hub 4. The cut-out 35 can be introduced into the hub as a slit, for example, with the slit also being able to extend in oblique or curved form with respect to the longitudinal axis 27 to achieve a spiral revolution of the conveying element about the hub.

A particularly inexpensive and simple manner of manufacture of the conveying elements is provided by the design in accordance with the invention of a rotor with corresponding conveying elements which moreover allows a simple compression and expansion of the conveying elements. The space requirements of the rotor on the transport into the operating position are minimized by the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A radially compressible and expandable rotor for a fluid pump having a hub and at least one conveying element which has a plurality of struts and a membrane interposed between two adjacent struts, wherein at least one first group of struts is pivotable from a closed configuration into an open configuration, wherein, in the open configuration, the at least one conveying element has a semi-elliptical shape, starting from a common base located in a cut-out formed in the hub.

2. A rotor in accordance with claim 1, wherein the plurality of struts are at least partly received in the cut-out in the closed configuration.

3. A rotor in accordance with claim 1, wherein the common base comprises a common pivot axis of the plurality of struts partly received in the cut-out.

4. A rotor in accordance with claim 3, wherein the common pivot axis passes through the cut-out and extends tangentially to a peripheral direction of the hub.

5. A rotor in accordance with claim 1, comprising two conveying elements wherein each have the plurality of struts, which are disposed opposite one another at a periphery of the hub and wherein each of the two conveying elements is at least partly received in a respective one of two cut-outs of the hub when each of the two conveying elements is in the closed configuration.

6. A rotor in accordance with claim 5, wherein each of the conveying elements lies along the hub at both sides of the respective cut-out and contacts the hub in the open configuration in each case.

7. A rotor in accordance with claim 1, wherein the membrane is inclined at least sectionally with respect to a rotor axis in the open configuration.

8. A rotor in accordance with claim 7,
wherein at least one strut is angled or curved out of a pivot plane of the struts at least over a part of its length with respect to further struts.

9. A rotor in accordance with claim 3, wherein the common pivot axis is a shaft and the struts are pivotably mounted on the shaft.

10. A rotor in accordance with claim 5,
wherein the two cut-outs at the hub are connected to one another in a throughgoing manner and form a passage opening of the hub.

11. A rotor in accordance with claim 1, wherein the pivotable struts are connected to one another by film hinges at their base.

12. A rotor in accordance with claim 1, wherein different struts having different lengths are provided.

13. A rotor in accordance with claim 1, wherein at least one rail is provided along the hub for reception of struts of the at least one conveying elements positioned along the hub in the open configuration.

14. A rotor in accordance with claim 1, wherein the struts pivot about an axis which is non-parallel to a longitudinal axis of the hub.

15. A rotor according to claim 1, wherein the at least one conveying element covers an angle of about 180 degrees in the open configuration.

\* \* \* \* \*